Nov. 6, 1962 W. E. SILVA Plant Pat. 2,191
ROSE PLANT
Filed July 31, 1961
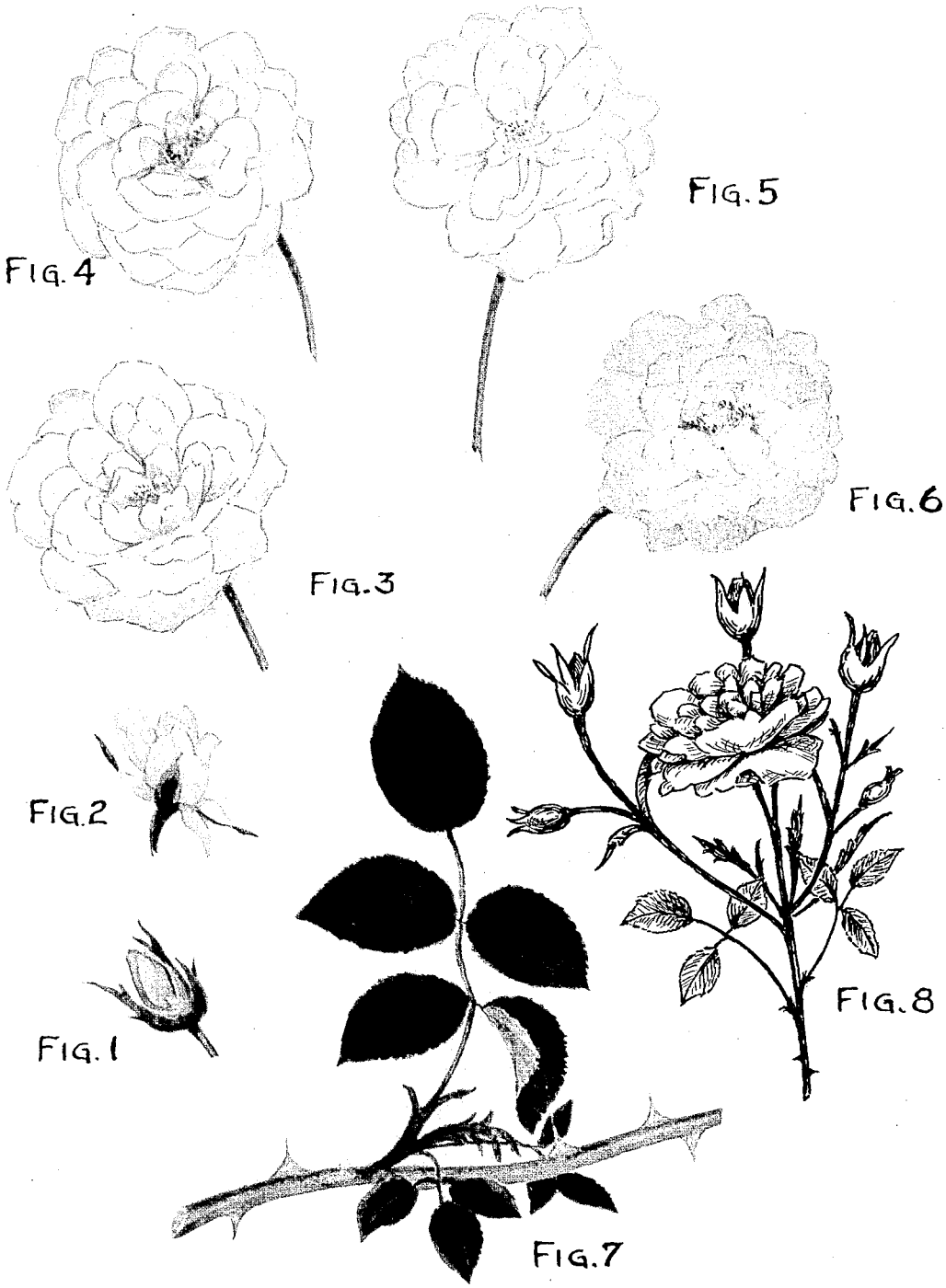
WITNESS
Addison E. Avery
INVENTOR
WILLIAM E. SILVA
by Rummler & Snow
ATTYS.

United States Patent Office

Plant Pat. 2,191
Patented Nov. 6, 1962

2,191
ROSE PLANT

William E. Silva, Sebastopol, Calif., assignor to Anthony Machine and Engineering Service, Inc., Millbrae, Calif., a corporation of California Filed July 31, 1961, Ser. No. 128,262
1 Claim. (Cl. 47—61)

This invention concerns a new and distinct variety of rose plant of the floribunda class and is the result of breeding efforts carried out by me and under my direction in my breeding grounds at Sebastopol, California, since 1955.

This new variety of rose plant resulted from a selected seedling developed by cross breeding "Masquerade" (Plant Patent 975), as the pollen parent, with "Maxine" (Plant Patent 1,879) as the seed parent and this new variety has been asexually propagated by me at Sebastopol, California and at San Jacinto, California. Successive propagation by cuttings, buds, and grafting, at both said locations, has proved the novel and distinctive characteristics of this new variety to hold true from generation to generation and to be permanently fixed.

The novel and distinctive characteristics of my new variety of rose plant reside in its multi-colored flowers which break continuously throughout the growing season and pass through four distinct color changes as the blooms age from first full opening to the final stage; its habit of blooming profusely from early spring through the fall; its prolific and vigorous growth habit with abundant foliage and flowers appearing in clumps on sturdy upright stems; the unusually and pleasantly strong fragance of the blooms; and the improved plant structure and tonality.

The flowers of my new variety are very double in form and appear to endure all types of weather. Their lasting quality is very good, both on the plant and as a cut flower, and they are extraordinarily fragrant throughout the life of the bloom. The new buds, when the sepals first divide, are of a reddish color with some petal margins of a yellow orange. As the petals begin to unfurl the color changes to a generally over-all yellow orange color with pink at some of the petal tips. When the flower is first fully opened, all but the outermost petals are yellow with tinges of pink and the outermost petals are generally orange pink with pink margins at their outer ends. As the flower matures the color of the petals changes to pink, beginning with the outer petals and progressing inwardly, some of the petals even fading to white at the base, the inner petals remaining generally yellow but becoming edged with pink to give the petals an orange cast. In the third stage of the flower all but the innermost petals have turned to pink with the outer petals having dark pink margins, fading to lighter pink toward the base. The very center of the flower still retains the orange-yellow color and the change to light pink to dark pink is progressive from the inner to the outer rows of petals. At the final stage only a small area of yellow remains at the center of the bloom and the bloom generally has an over-all mahogany red color—darkest in the outer rows of petals and the inner rows having a light purple cast. Also, in the final stage some of the inner petals have nearly white edges.

This new variety of rose plant has been carefully observed and tested at Sebastopol and at San Jacinto, California and has been observed to be resistant to common rose diseases, such as mildew and black spot, and since no diseases have been observed in the trials and tests of the new variety it is believed that the plant is inherently resistant to common rose diseases.

The beforementioned and other distinctive characteristics of my new variety of rose plant and the several stages of its blooms are illustrated in the accompanying full color drawings in which:

FIGURE 1 is a view showing a new bud when the sepals first divide.

FIG. 2 is a similar view showing the bud as the petals begin to unfurl.

FIG. 3 is a three-quarter face view showing the bloom at its first full open stage.

FIG. 4 is a face view showing the bloom at its second stage, when the color of the outer petals has become pink while the center portion of the flower is still mainly yellow.

FIG. 5 is a similar view showing the third stage of the bloom, when the color is generally pink with only the innermost petals retaining the yellow color.

FIG. 6 is a similar view of the bloom in its final, mahogany color stage.

FIG. 7 is a view showing the wood, thorns and foliage of the new plant, and

FIG. 8 is a pen drawing illustrating the floribunda type of growth of the new plant.

The following is a more detailed description of my new rose plant:

*The Plant*

Origin: Seedling.
Parentage:
*Seed parent.*—"Maxine," Plant Patent 1,879.
*Pollen parent.*—"Masquerade," Plant Patent 975.
Classification: Floribunda.
Form: Low growing bush.
Height: About two feet.
Growth: Prolific, vigorous, sturdy and upright; branching from new low wood.
Foliage:
*Leaves.*—Abundant. 5 leaflets, pinnately compound.
*Shape of leaflet.*—Ovoid and serrated.
*Size of leaf.*—Approx. 4 inches long x approx. 2 inches wide.
*Texture.*—Leathery, prominent ribs with 10 veins.
*Petioles.*—On leaves—one-half inch long.
*Rachis.*—Firm.
*Thorns.*—About one-third inch long. Red at base and with whitish tips.

*Bud*

Size: About one-half inch in diameter and one inch long.
Form: Long-ovoid, pointed.
Opens slowly.
Color: Red-pink to orange when sepals first divide. Yellow orange when petals begin to unfurl.
Sepals: Spear shaped, upstanding and branched. Sepals do not curl back.
Calyx: Broad, pear-shaped, does not split and has a smooth aspect.
Peduncle: Erect and strong, about 2 to 3 inches long.

*Flower*

Blooming habit: Continuously and profusely from early spring through fall. Has tendency to give fewer blooms in fall.
Size: Medium. 1½ inches to 2 inches in diameter.
Borne: In clusters.
Shape: Cup-shaped when bloom first opens.
Petalage: 35 petals arranged in imbricated rows. Petals stay on stem for 5 to 8 days.
Petaloids: Small in number. One inch long. Yellow orange in color.
Peduncle: Sturdy and upright, 2 inches in length.
Texture: Soft.
Appearance: Shiny.
Effect of weather: Flower will endure all weather occuring during normal blooming season.
Persistence: Does not hang on and dry.
Fragrance: Very fragrant.
Lasting quality: Very good on plant and as a cut flower.
Color: Each bloom has four distinctive color stages. When bloom first opens color is generally yellow to yellow orange with pink at tips of outermost petals (FIG. 3). This then changes to generally pink outer rows of petals and yellow inner rows with inner rows of petals tipped with pink margins (FIG. 4). Third stage is substantially all pink with yellow only in innermost rows of petals (FIG. 5). Fourth stage generally mahogany red with small area of yellow at center and with some of inner petals having white margins (FIG. 6).

*Genital Organs*

Stamens:
*Anthers.*—85 to 95 in number, 1/16 inch long and arranged circularly.
*Filaments.*—1/16 inch long. Yellow in color.
Pollen: Yellow in color.
Pistils: 60 in number, about 1/10 inch long.
Stigmas: Yellow in color.
Ovaries: Very small.

*Fruit*

Fertile, round in shape, and green in color at maturity.

The color characteristics of my new variety of rose plant, according to Maerz and Paul Dictionary of Color, are as follows:

| | Plate | Letter | No. |
|---|---|---|---|
| Flower: | | | |
| First Stage (FIG. 3)— | | | |
| Center petals—Light Yellow | 9 | K | 1 |
| to | 9 | L | 2 |
| to | 9 | J | 7 |
| Outer petals—edged with Pink | 1 | F | 2 |
| to | 1 | G | 4 |
| Second Stage (FIG. 4)— | | | |
| Center petals—Light Yellow | 9 | K | 1 |
| to | 9 | K | 5 |
| Outer petals—Pink | 1 | I | 2 |
| to | 1 | K | 3 |
| Third Stage (FIG. 5)— | | | |
| Small center area—Yellow | 10 | L | 6 |
| Main body of petals—Pink | 1 | E | 4 |
| to | 1 | D | 6 |
| Nearly White areas at edges of some petals | 1 | B | 1— |
| Fourth Stage (FIG. 6)— | | | |
| Small area at center—Yellow | 9 | L | 5 |
| Light Purple cast on petals with White areas | 50 | F | 3 |
| to | 50 | K | 2 |
| to | 3 | K | 4 |
| White areas on some petals | 1 | B | 1 |
| In all 4 stages each bloom has a Pale Green color at very center | 19 | K | 1 |
| Stems: On all 4 stages of bloom | 15 | A | 12+ |
| Leaf: | | | |
| Top side—Green | 23 | L | 7 |
| Under side—Green | 21 | J | 6 |
| Thorns: Base of large thorns—Red | 5 | L | 7 |

Having thus disclosed my new rose plant variety, I claim:

A new and distinct variety of rose plant of the floribunda type, substantially as herein shown and described, characterized as to novelty by its medium sized blooms each of which when opened passes through four distinct stages of coloration, beginning with a predominantly yellow orange color in the freshly opened bloom, changing next to pink in the outer rows of petals with the yellow orange color remaining in the central area petals, then changing to a predominantly pink color for all of the petals except those at the center of the flower which remain yellow-orange, and finally changing to a substantially over-all mahogany red color as the flower reaches full maturity; and further characterized by its continuous and profuse blooming habit from early spring until fall; and the extraordinary fragrance of its blooms which persists throughout all stages of their color change.

No references cited.